(12) United States Patent
Goyal

(10) Patent No.: US 11,826,518 B2
(45) Date of Patent: *Nov. 28, 2023

(54) SYSTEM AND METHODS FOR INTRACRANIAL VESSEL ACCESS

(71) Applicant: Mayank Goyal, Calgary (CA)

(72) Inventor: Mayank Goyal, Calgary (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/457,006

(22) Filed: Nov. 30, 2021

(65) Prior Publication Data

US 2022/0080152 A1    Mar. 17, 2022

Related U.S. Application Data

(63) Continuation of application No. 16/578,187, filed on Sep. 20, 2019, now Pat. No. 11,219,742, which is a continuation of application No. 14/809,867, filed on Jul. 27, 2015, now Pat. No. 10,456,552.

(60) Provisional application No. 62/029,684, filed on Jul. 28, 2014.

(51) Int. Cl.
*A61M 25/00* (2006.01)
*A61M 25/01* (2006.01)

(52) U.S. Cl.
CPC .... *A61M 25/0023* (2013.01); *A61M 25/0068* (2013.01); *A61M 25/01* (2013.01); *A61M 2025/0042* (2013.01)

(58) Field of Classification Search
CPC .......... A61M 25/0023; A61M 25/0021; A61M 25/0026; A61M 25/0067; A61M 25/0068; A61M 25/0102; A61M 25/01; A61M 25/09025; A61M 25/09041; A61M 25/0028; A61M 25/0032; A61M 25/0113; A61M 25/0662; A61F 2/966; A61F 2/962; A61F 2/013; A61B 2017/22044; A61B 2017/00991; A61B 2017/347; A61B 17/3417
See application file for complete search history.

(56) References Cited

U.S. PATENT DOCUMENTS

| | | | |
|---|---|---|---|
| 4,571,240 A | 2/1986 | Samson et al. | |
| 4,994,033 A | 2/1991 | Shockey et al. | |
| 5,257,979 A | 11/1993 | Jagpal | |
| 5,303,714 A | 4/1994 | Abele et al. | |

(Continued)

OTHER PUBLICATIONS

2015 AHA/ASA Focused Update of the 2013 Guidelines for the Early Management of Patients With Acute Ischemic Stroke Regarding Endovascular Treatment: A Guideline for Healthcare Professionals from the American Heart Association/American Stroke Association Powers et al. on behalf of the American Association Stroke Council Stroke. 2015; STR.0000000000000074 published online before print Jun. 29, 2015, doi:10.1161/STR.0000000000000074.

(Continued)

*Primary Examiner* — Emily L Schmidt
*Assistant Examiner* — Alexandra Lalonde
(74) *Attorney, Agent, or Firm* — Inskeep IP Group, Inc.

(57) ABSTRACT

The invention relates to systems and methods for intracranial vessel access. In particular, a system including a co-axial combination of a steerable variable thickness microwire operatively supporting a tapered larger bore support and larger bore distal access catheter is described. Methods of advancing the intracranial access system through the vasculature are also described.

20 Claims, 6 Drawing Sheets

(56) References Cited

U.S. PATENT DOCUMENTS

| | | |
|---|---|---|
| 5,318,032 A | 6/1994 | Lonsbury et al. |
| 5,549,601 A | 8/1996 | McIntyre et al. |
| 5,693,029 A | 12/1997 | Leonhardt |
| 6,142,958 A | 11/2000 | Hammarström et al. |
| 6,228,052 B1 | 5/2001 | Pohndorf |
| 6,309,379 B1 | 10/2001 | Willard et al. |
| 6,475,244 B2 | 11/2002 | Herweck et al. |
| 6,579,260 B2 | 6/2003 | Maki et al. |
| 6,673,025 B1 | 1/2004 | Richardson et al. |
| 6,685,672 B1 | 2/2004 | Forman |
| 6,706,055 B2 | 3/2004 | Douk et al. |
| 6,716,183 B2 | 4/2004 | Clayman et al. |
| 6,723,064 B2 | 4/2004 | Babaev |
| 6,761,708 B1 | 7/2004 | Chiu et al. |
| 6,773,448 B2 | 8/2004 | Kusleika et al. |
| 7,118,539 B2 | 10/2006 | Vrba et al. |
| 7,242,977 B2 | 7/2007 | Partridge et al. |
| 7,381,200 B2 | 6/2008 | Katoh et al. |
| 8,043,279 B2 | 10/2011 | Hisamatsu et al. |
| 8,801,670 B2 | 8/2014 | Drontle et al. |
| 9,211,132 B2 | 12/2015 | Bowman |
| 2002/0087076 A1 | 7/2002 | Meguro et al. |
| 2010/0305475 A1* | 12/2010 | Hinchliffe ......... A61M 25/0905 600/585 |
| 2013/0165873 A1 | 6/2013 | Morriss et al. |
| 2013/0281788 A1 | 10/2013 | Garrison |
| 2014/0180246 A1 | 6/2014 | Comerota et al. |
| 2015/0297250 A1 | 10/2015 | Farhat et al. |
| 2016/0015935 A1* | 1/2016 | Chan ................... A61M 25/09 604/528 |

OTHER PUBLICATIONS

Goyal et al. *Randomized Assessment of Rapid Endovascular Treatment of Ischemic Stroke*, New England Journal of Medicine, DOI 10.1056/NE/Moa1414905, Feb. 11, 2015.

Saver et al. (Apr. 17, 2015) *Stent-Retriever Thrombectomy after Intravenous t-PA vs. T-PA Alone in Stroke*, New England Journal of Medicine, DOI:10.1056/NEJMoa1415061, Apr. 17, 2015.

\* cited by examiner

SYSTEM AND METHODS FOR INTRACRANIAL VESSEL ACCESS

RELATED APPLICATIONS

This application is a continuation of and claims priority to U.S. patent application Ser. No. 16/578,187, filed Sep. 20, 2019, entitled System And Methods For Intracranial Vessel Access, which is a continuation of claims benefit of and priority of U.S. patent application Ser. No. 14/809,867, filed Jul. 27, 2015, entitled System And Methods For Intracranial Vessel Access (now U.S. Pat. No. 10,456,552 issued Oct. 29, 2019), which claims benefit of and priority to U.S. Provisional Application Ser. No. 62/029,684 filed Jul. 28, 2014 entitled System And Methods For Intracranial Vessel Access, all of which are hereby incorporated herein by reference in their entireties.

FIELD OF THE INVENTION

The invention relates to systems and methods for intracranial vessel access. In particular, a system including a co-axial combination of a steerable variable thickness microwire operatively supporting a tapered larger bore support and larger bore distal access catheter is described. Methods of advancing the intracranial access system through the vasculature are also described.

BACKGROUND OF THE INVENTION

Acute ischemic stroke (AIS) is caused by a sudden blockage to one of the large intracranial vessels in the brain by a blood clot that moves through the intracranial vessels and where it becomes lodged within a narrowing vessel thus cutting off blood flow to a portion of the brain. AIS is usually a devastating disease that unless quickly treated to re-establish blood flow to the brain can result in significant impairment of a patient's brain function.

Importantly, recent studies including "Randomized Assessment of Rapid Endovascular Treatment of Ischemic Stroke" published on Feb. 11, 2015, at NEJM.org, and "Stent-Retriever Thrombectomy after Intravenous t-PA vs. t-PA Alone in Stroke" published on Apr. 17, 2015, at NEJM.org, have shown that patient outcome is significantly improved by removing the blood clot quickly and safely. The effect of these studies has been that endovascular treatment of stroke is now the standard of care as endorsed by the American Heart Association/American Stroke Association (see "2015 AHA/ASA Focused Update of the 2013 Guidelines for the Early Management of Patients With Acute Ischemic Stroke Regarding Endovascular Treatment—A Guideline for Healthcare Professionals From the American Heart Association/American Stroke Association; www.stroke.ahajournals.org: ((*Stroke.* 2015; 46:000-000).

Recanalization are procedures that are used to remove the blood clot by guiding recanalization equipment through the blood vessels of the brain under x-ray guidance. In a recanalization procedure, access to the vascular system is typically obtained in the patient's groin region by entering the common femoral artery and advancing a steerable wire within a coaxial balloon guide catheter through the vascular system to access the carotid artery. Often there may be a diagnostic preshaped catheter with the balloon guide catheter to allow access to the relevant branch from the aorta.

For the purposes of general illustration, and with reference to FIG. 1, a simple schematic representation of a section of brain vascular anatomy is shown. As shown in FIG. 1, the ophthalmic segment of the carotid artery OA is shown having a tortuous segment 5. Distal to the ophthalmic artery is the intracranial internal carotid artery IICA, the anterior cerebral artery ACA, the M1 segment of the middle cerebral artery and the M2 segment of the middle cerebral artery. A blood clot or occlusion Y is shown within the M1 segment.

Usually, when the physician has entered the carotid artery with the catheter, the intracranial occlusion is confirmed by injecting a bolus of xray dye into the patient and taking xray pictures that then assist the physician in accurately determining the location and size of the occlusion in order that the microwire and microcatheter are advanced to the desired position relative to the occlusion.

At this stage, when a microwire has been advanced to the clot, there are varying technologies and techniques that can be used to recanalize the blood vessel.

The most commonly used technology uses a self-expanding stent or stent retriever as a means to withdraw the thrombus responsible for the occlusion. In this procedure, a microcatheter with the help of the microwire is advanced beyond the clot using xray guidance. A guide catheter having a balloon will typically also be advanced to a position in the internal carotid artery in the neck. Subsequently, the self-expanding stent is advanced into the microcatheter and is gently deployed across the occlusion by withdrawing the microcatheter and unsheathing the stent. Usually after deployment of the stentriever there is some degree of forward flow. After waiting for a few minutes the thrombus gets entangled in the tines of the stent retriever. At this stage, the balloon in the guide catheter is inflated to prevent antegrade (forward) flow in the vessels, and the stent is withdrawn while applying suction (reversal of flow direction) at the guide catheter in the neck. The clot is thereafter removed through the guide catheter.

This approach has a few disadvantages including that the procedure does not always work for various reasons. For example, depending on the anatomy of the patient, applying suction pressure at the neck sometimes does not get transmitted to the clot particularly if there are other branches (from a patent circle of Willis) that may provide blood flow in a way that the suction pressure is not transmitted to the occluded vessel. In addition, there is also a potential for the clot to fragment and move into distal vessels. Further still, managing and placing balloon guide catheters can be technically challenging and potentially time consuming. In addition, self-expanding stents are expensive.

As a result, there is a move towards making catheters with a larger inner lumen that are flexible enough that they can be advanced into the brain vessels (typically the middle cerebral artery) and into a position such that the catheter can be used to directly suck the clot through the catheter rather than using an expandable stent. This procedure overcomes some of the disadvantages including applying suction pressure directly to the clot in a manner that is not dependent on the patient's anatomy. In addition, the costs will be lower if a stent is not used and this procedure may also save time. Local suction may also reduce the likelihood of clot fragmentation.

However there are significant limitations to the current generation of large bore distal access catheters (DACs). One of these is the ability of these catheters to move through those blood vessels having a significant curvature. In particular, it is known that most strokes occur in older people where the tortuosity of certain blood vessels may be greater than the same blood vessels of a younger person due to age-related changes in the vasculature. Also, the inner surface of the vessels in an older person may not be as smooth because of atherosclerotic disease. Importantly, both of these conditions can compound the problem of moving catheters through the vasculature of a stroke patient.

As shown in FIGS. 2 and 2A, the procedure of inserting a large bore distal access catheter 18 typically involves the manipulation of a tri-axial system comprising a microwire 12a inside a microcatheter 12b inside a distal access catheter (DAC) 18 through the vasculature. Initially, the microwire and microcatheter are placed in the carotid artery in the neck and are then advanced to beyond the clot. Using the microwire and microcatheter as support, the distal access catheter is then advanced forward to the desired position adjacent the clot. In certain locations, this procedure does not often work properly as the distal access catheter gets stuck around tight bends especially in the ophthalmic bend of the internal carotid artery as shown in FIG. 2A. That is, the outer edge 18a of the DAC may be pushed into the outer surface of the ophthalmic bend which often leads to it becoming stuck. This problem is compounded by the difference in diameter of the distal end of the DAC relative to the diameter of the microcatheter 12b that creates a gap 17. If the DAC gets stuck, this results in delays.

One solution that has been proposed to address this problem of the DAC getting stuck is to deploy the stentriever through the microcatheter and use the friction of the stentriever against the vessel and clot as leverage to be able to manipulate the distal access catheter through the bend. That is, by a combination of gently pushing and pulling the stentriever and DAC, the DAC can be advanced around the tight curvature of the ophthalmic bend. While this can be successful, this is disadvantaged by the significant cost increase of using a stent and it can also be time consuming. Moreover, given the differences in size between the DAC and microcatheter, the gap 17 may prevent forward movement of the DAC over the microcatheter as the distal end of the DAC cannot be bent enough within the tight curve.

Accordingly, there has been a need for a system that in particular aids the movement of a larger bore catheter (i.e. a distal access catheter) through the vasculature and particularly regions of the vasculature having a high tortuosity.

SUMMARY OF THE INVENTION

In accordance with the invention, there is provided a system for intracranial access through a patient's vasculature to access an intracranial occlusion, the system including a variable diameter guide and support system for steering and advancing a flexible line of material through the patient's vasculature, the variable guide and support system having a distal tip region and an expanded section wherein the expanded section has a distal tapering surface connecting the distal tip region to the expanded section and wherein the expanded section proximal to the distal tapering surface has a cylindrical surface having an outer diameter greater than the diameter of the distal tip region.

In another embodiment, the variable diameter guide and support system includes a proximal support section having a flexible line of material having a diameter less than the cylindrical surface and a strength sufficient to advance the inner guide and support system through the patient's vasculature.

In another embodiment, a distal access catheter is operatively connected to the variable diameter guide and support system and wherein the distal access catheter has a distal inner diameter substantially corresponding to the diameter of the cylindrical surface and wherein the distal access catheter can move coaxially relative to the cylindrical surface.

In various embodiments, the cylindrical surface has an axial length of 6-10 cm and/or the distal tapering surface has an axial length of 4-6 cm and/or the diameter of the cylindrical surface is about 0.058-0.075 inches and/or the diameter of the distal tip section is about 0.014-0.016 inches and/or the proximal support section has a diameter of about 0.035 inches.

In one embodiment, the distal tip section and proximal support section are connected together and the expanded section is independently and coaxially moveable with respect to the distal tip section and proximal support section.

In yet another embodiment, the distal access catheter has an outer diameter of 0.065-0.075 inches.

In a further embodiment, the expanded section has a flexibility enabling movement through a vessel having a 1-1.5 cm diameter.

In another aspect, the invention provides a method of accessing an intracranial occlusion through a patient's vasculature comprising the step of: a) advancing an inner guide and support system through the patient's vasculature, the inner guide and support system having a distal tip region and an expanded section wherein the expanded section has a distal tapering surface connecting the distal tip region to the expanded section and wherein the expanded section proximal to the distal tapering surface has a cylindrical surface having an outer diameter greater than the diameter of the distal tip region; and wherein the inner guide and support system is operatively connected to a distal access catheter having a distal inner diameter substantially corresponding to the diameter of the cylindrical surface and wherein the distal access catheter can move coaxially relative to the cylindrical surface and b) manipulating the inner guide and support system and distal access catheter through the patient's vasculature by a combination of torsional movements of the inner guide and support system and coaxial movements of the inner guide and support system relative to the distal access catheter to move the distal access catheter through regions of the patient's vasculature having a high tortuosity.

BRIEF DESCRIPTION OF THE DRAWINGS

Various objects, features and advantages of the invention will be apparent from the following description of particular embodiments of the invention, as illustrated in the accompanying drawings. The drawings are not necessarily to scale, emphasis instead being placed upon illustrating the principles of various embodiments of the invention. Similar reference numerals indicate similar components.

DETAILED DESCRIPTION OF THE INVENTION

Various aspects of the invention will now be described with reference to the figures. For the purposes of illustration, components depicted in the figures are not necessarily drawn to scale. Instead, emphasis is placed on highlighting the various contributions of the components to the functionality of various aspects of the invention. A number of possible alternative features are introduced during the course of this description. It is to be understood that, according to the knowledge and judgment of persons skilled in the art, such alternative features may be substituted in various combinations to arrive at different embodiments of the present invention.

In particular, intracranial access systems (IAS) 10 that can facilitate the movement of a larger diameter catheter through sections of a patient's vasculature having a high curvature are described.

Figure 1:
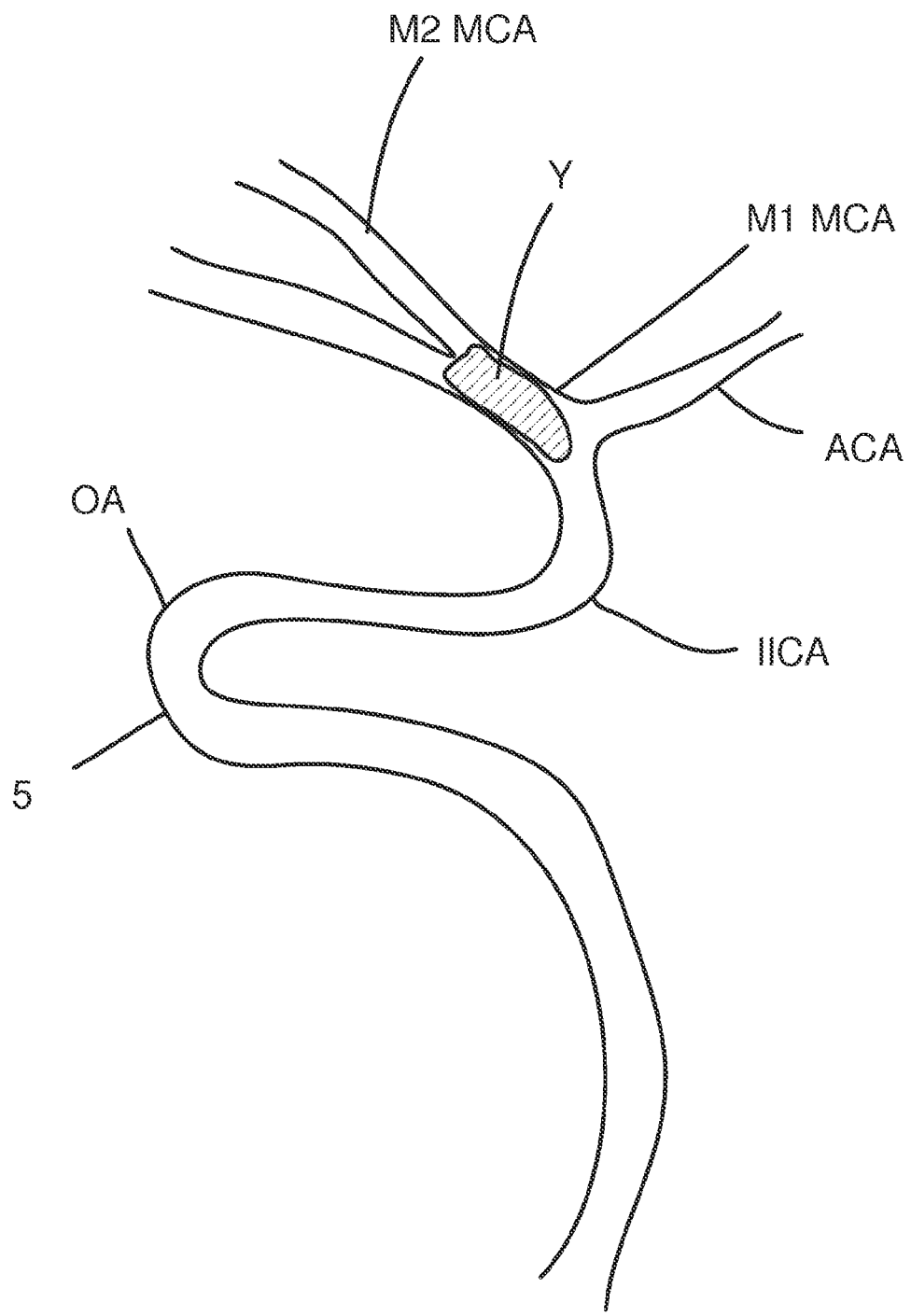
FIG. 1 is a schematic sketch of brain vascular anatomy showing the ophthalmic artery (OA), intracranial internal carotid artery (IICA), anterior cerebral artery (ACA), M1 segment of the middle cerebral artery and M2 segment of the middle cerebral artery.
Figure 2:
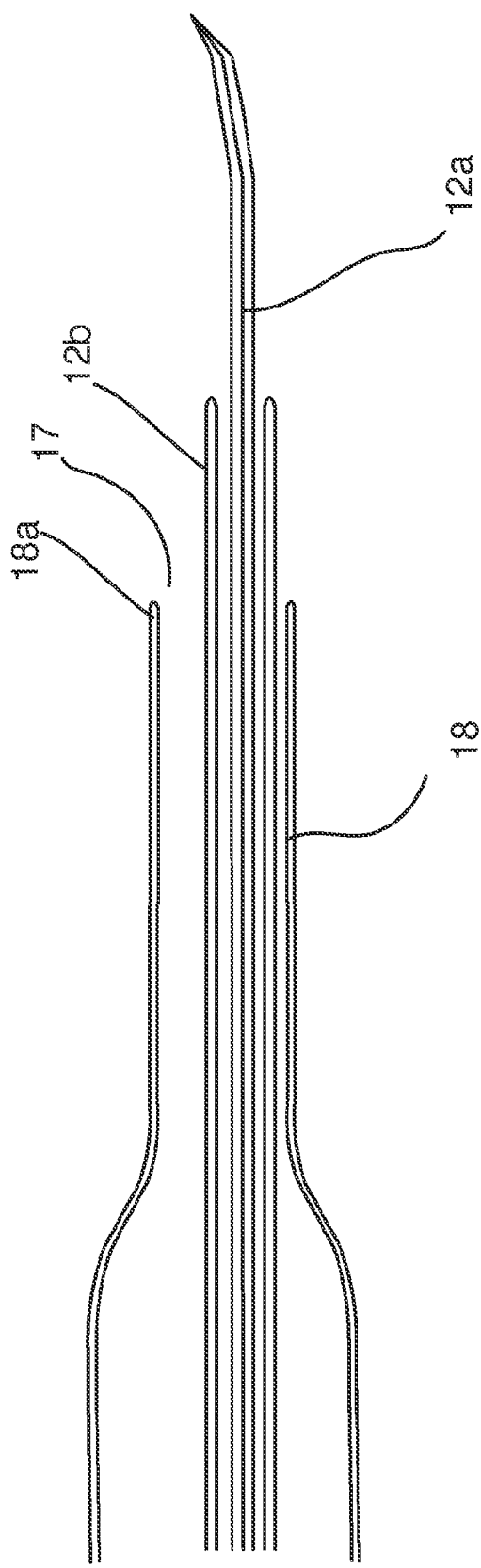
FIG. 2 is a sketch of a typical microwire, microcatheter and distal access catheter that may used for recanalization procedures in accordance with the prior art.
Figure 2A:
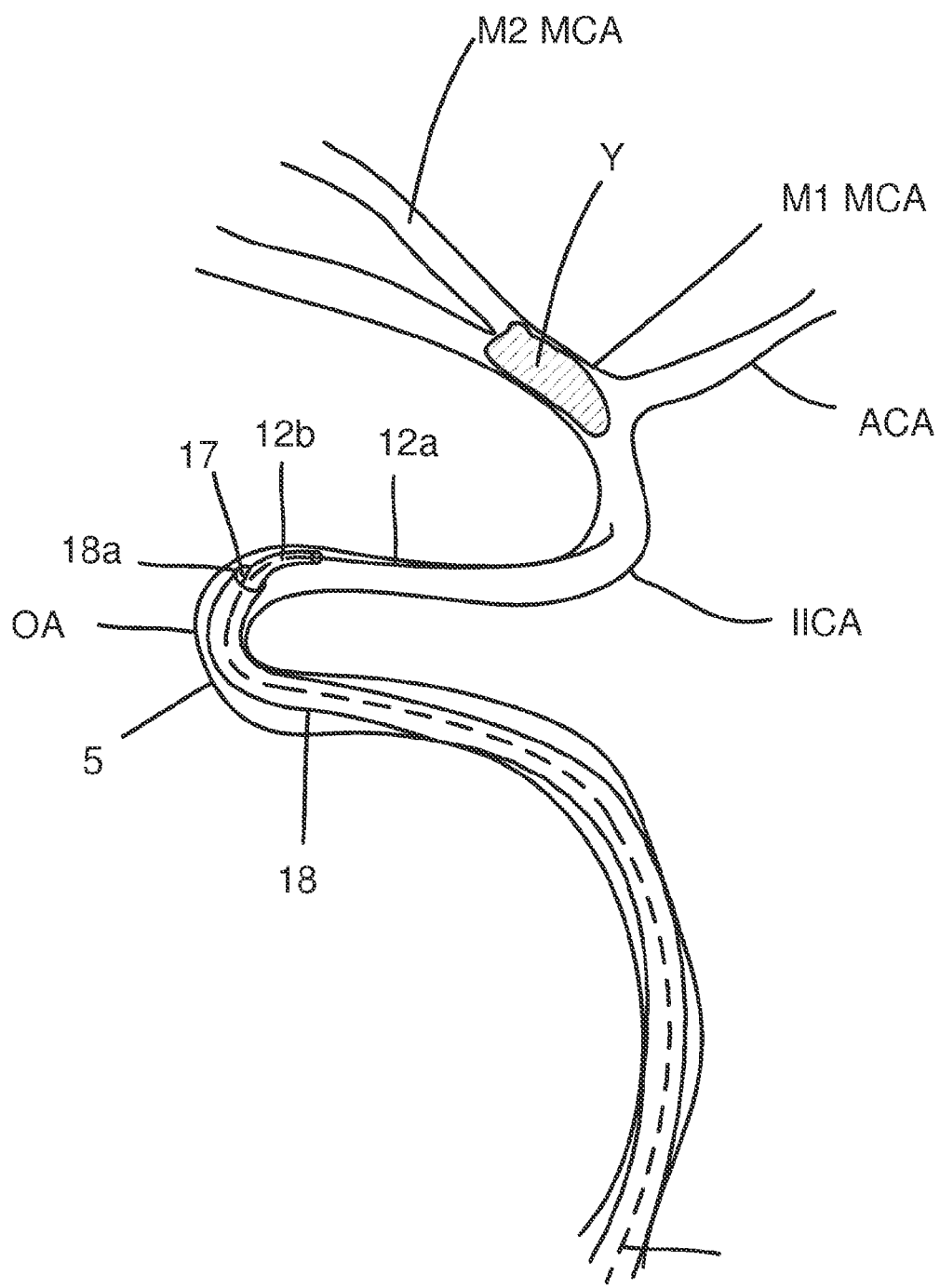
FIG. 2A is a sketch of the ophthalmic bend illustrating the problem of advancing a DAC over a microcatheter in a region of high tortuosity.
Figure 3:
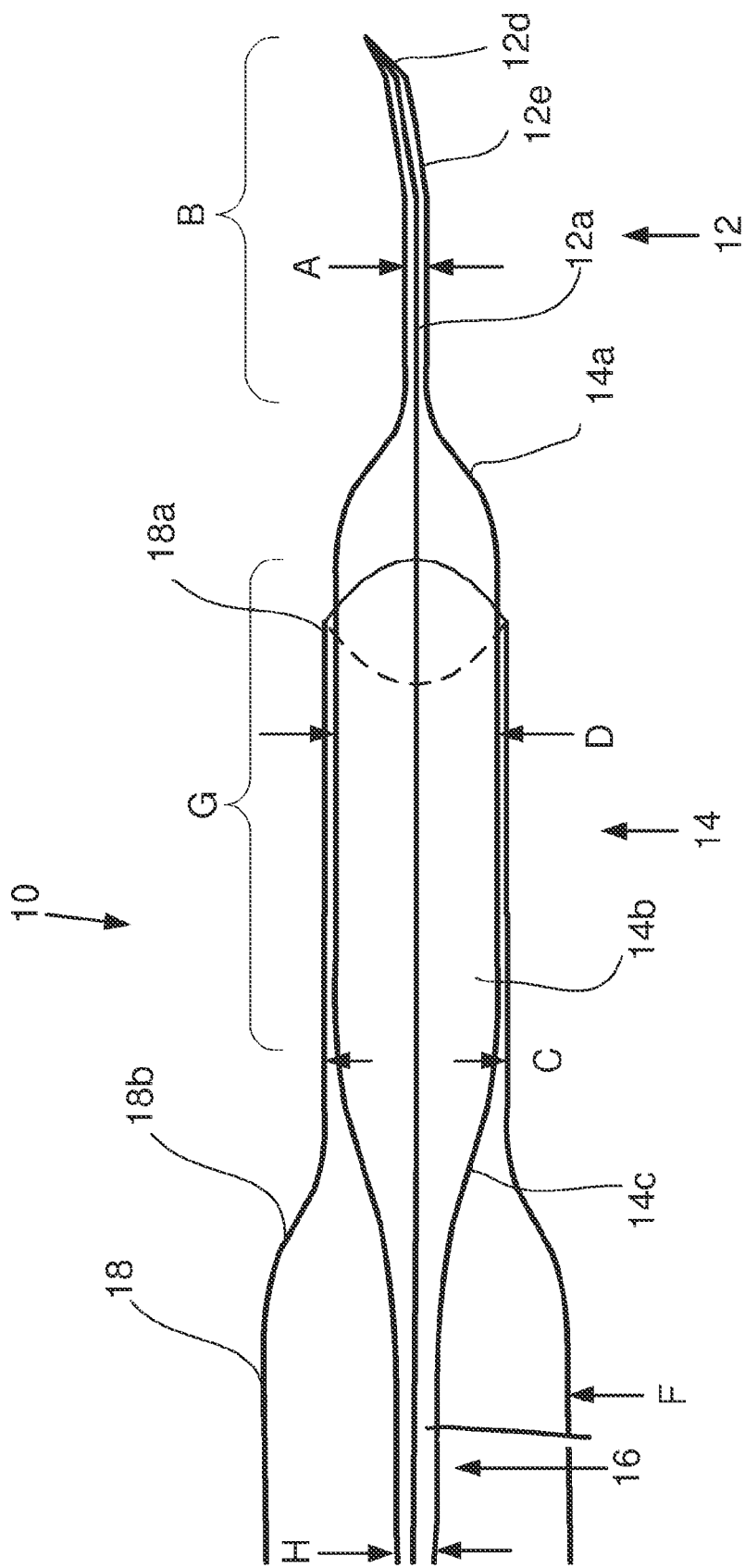
FIG. 3 is a sketch of an intracranial access system (IAS) in accordance with one embodiment of the invention.

In a first embodiment, as shown in FIG. 3, the intracranial access system 10 comprises a distal tip section 12, an expanded section 14 and a proximal support section 16. The IAS may include a distal access catheter 18. As described in greater detail below, a central section of the IAS 14 *b* is of a diameter that fits into and supports a distal end 18*a* of the DAC. The IAS will typically have a total length of about 2 m.

Distal Tip Section 12

The distal tip section 12 is generally a thin wire having a pre-formed or formable tip 12*d* enabling intracranial access. The wire will have an appropriate atraumatic coating 12*e* for intracranial use and will typically have an outer diameter A of 0.014-0.016 inch. The length B of distal tip section will be in range of 12-24 cm. The internal wire may extend the entire length of IAS.

Expanded Section 14

The expanded section 14 provides a tapered transition from the narrower distal tip section 12 to the wider inner diameter C of a DAC 18. In the context of this description, a "taper" is generally referred to as a change in diameter from one section of the IAS to another. That is, a taper implies a narrowing of diameter from a thicker region or a widening of diameter from a narrower region to a thicker region. The purpose of the expanded section is to prevent separation of the distal edge 18*a* of the DAC from the narrower distal tip section 12 as the distal region is being advanced and particularly as the distal region and DAC are being moved through areas of high vascular curvature.

As shown, the expanded section 14 includes a distal tapered section 14*a*, a cylindrical central section 14*b* and a proximal tapered section 14*c*. The central section 14*b* will have an outer diameter D generally corresponding to the inner diameter C of the distal end of the DAC. As shown, the DAC may also include a DAC tapered section 18*b* that transitions the DAC from a narrower distal diameter C to a wider proximal diameter F.

Importantly, the IAS (namely the distal tip, expanded and proximal support sections) and DAC can move independently of each other. The IAS is steerable. It would be expected that a skilled operator would advance the IAS first and subsequently advance the DAC over the IAS. The configuration would be maintained in a way that generally the distal end of the DAC would remain fixed in relation to expanded section 14 of the IAS to allow for smooth transition.

As can be seen, the central section 14 has a length G sufficiently long to enable this coaxial movement without causing the separation of the expanded section 14 from the distal inner diameter C of the DAC. In practice, the central section with have a length G of approximately 8 cm. The total length of the expanded section 14 between the distal tip section 12 and proximal support section 16 will be about 12-15 cm. Thus, each of the tapered sections 14*a* and 14*c* will be about 2-4 cm long.

The outer diameter D of the central section 14*b* will be approximately 0.058 inches and will be capable of moving through a curve having a 1-1.5 cm diameter. The central section 14*b* is sufficiently strong in the radial direction while being bent to prevent separation of the DAC distal end 18*a* from the expanded section while moving around a tight curve. The central portion may have additional coating such as a hydrophilic coating to reduce friction.

The central section 14*b* and tapers may be a spiral wire and/or a plastic/rubber section having sufficient flexibility to enable bending and movement through a tight curve and sufficient radial strength to prevent separation as described above. In the case of a spiral wire, the central section may be formed from the same wire as the distal tip section or be a separate wire co-axially wound on an inner wire. In the case of a plastic/rubber section, the central section may be cast on an inner wire. In some embodiments, the central section and taper may be a combination of both coaxially wound wire and cast plastic/rubber.

Proximal Support Section 16

The proximal support section 16 will typically have an outer diameter H of about 0.035 inches and have sufficient axial compressive strength enable the distal tip section 12 to be pushed forward and sufficient torsional strength for turning of the distal tip section 12.

Figure 4:
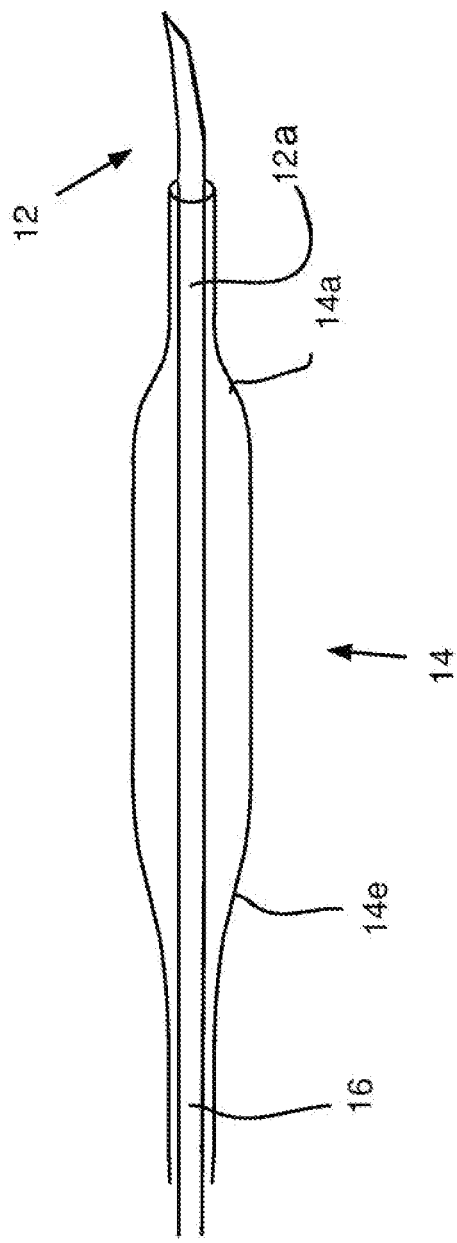
FIG. 4 is a sketch of a multisegment coaxial wire having an expanded section in accordance with one embodiment of the invention, where an inner core is moveable within the outer part of the wire. This outer part may be a highly flexible wire or a variable diameter catheter.

As shown in FIG. 4, in an alternate embodiment, the distal tip region 12 and proximal support region 16 can be additionally coaxially moved relative to the expanded section 14. Thus, in this embodiment, the expanded region 14 forms a cover over the proximal support region having a tapered region proximal support section 14*e* that extends proximally and that enables the physician to independently slide these separate components relative to one another. In this embodiment expanded section 14 may be made of metal or polymers or a combination (using technologies used in making wires and microcatheters and DACs). As in the embodiment illustrated by FIG. 3, in this alternate embodiment, a DAC may be preloaded onto the inner components.

Further, the underlying wire 12*a* can be exchangeable so that if needed, once the distal access catheter is in place, the outer thicker part of the wire 12*a* can be removed and the underlying thinner wire could still be used for stentriever purposes if needed.

Figure 3A:
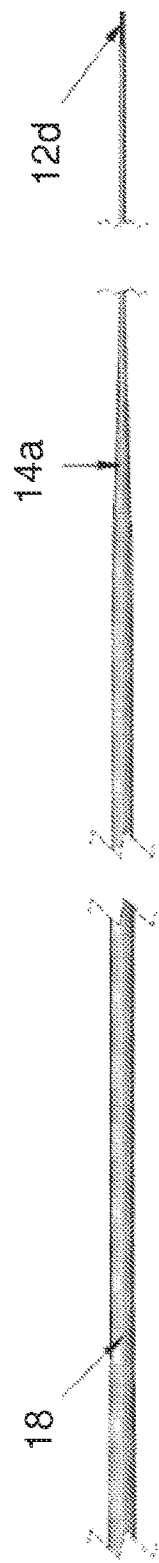
FIGS. 3A, 3B, 3C and 3D are side views of an assembled IAS (3A), distal access catheter (3B), expanded section (3C) and microwire (3D) in accordance with one embodiment of the invention.
Figure 3B:
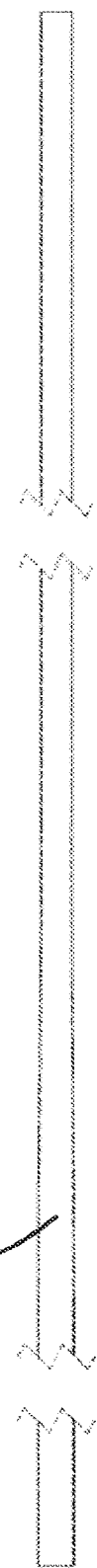
Figure 3C:
Figure 3D:

FIG. 3A shows an assembly of an IAS with FIGS. 3B, 3C and 3D showing an outer DAC 18, expanded section 14 and inner wire 12*a*.

Methods of Use

As described above, the IAS may be used to access an intracranial occlusion through a patient's vasculature. Generally, after the surgeon has gained access to the patient's vasculature, the following general steps are followed:
  a. advancing an inner guide and support system having a distal tip region and an expanded section wherein the expanded section has a distal tapering surface connecting the distal tip region to the expanded section and wherein the expanded section proximal to the distal tapering surface has a cylindrical surface having an outer diameter greater than the diameter of the distal tip region through the patient's vasculature together with a distal access catheter having a distal inner diameter substantially corresponding to the diameter of the cylindrical surface and wherein the distal access catheter can move coaxially relative to the cylindrical surface.
  b. manipulating the inner guide and support system and distal access catheter through the patient's vasculature by a combination of torsional movements of the inner guide and support system and coaxial movements of the inner guide and support system relative to the distal access catheter to move the distal access catheter through regions of the patient's vasculature having a high tortuosity.

IAS Advantages

Noted advantages of this solution are:
  a. As noted, if the IAS is preloaded into the distal access catheter, preparation time for surgery will be reduced.
  b. The system precludes the need for using a microcatheter or microwire thus saving money.
  c. If the clot can be successfully removed just by sucking through the distal access catheter, it would obviate the need for an expensive stent retriever.
  d. The IAS system overcomes the current problem of distal access catheters getting caught in tortuous curves especially in older patients with atherosclerotic vessels.

Units of measure used in this specification are consistent with the units used in the field of endovascular surgery. That is, both imperial and metric units are used where lengths are typically expressed in metric units while diameters are expressed in imperial units.

Although the present invention has been described and illustrated with respect to preferred embodiments and preferred uses thereof, it is not to be so limited since modifications and changes can be made therein which are within the full, intended scope of the invention as understood by those skilled in the art.

What is claimed is:

1. A system for accessing vasculature of a patient, comprising:
  an inner guide member having a proximal support section, a distal expanded section located distally of the proximal support section, and a guidewire passage extending between a proximal end and distal end of the inner guide member;
  the proximal support section having a first outer diameter;
  the distal expanded section having a second outer diameter that is larger than the first outer diameter of the proximal support section; and,
  the distal expanded section comprising an elongated shape with a proximal surface and a distal surface that taper in diameter in a substantially uniform manner;
  where in an operational configuration, the proximal end of the inner guide member is external to the patient and is slidable relative to a distal access catheter and to a guidewire positioned through the guidewire passage,
  where in the operational configuration the proximal surface of the distal expanded section is within the distal access catheter and the distal surface of the distal expanded section is outside of the distal access catheter such that a first gap between the distal expanded section and the distal access catheter is less than a second gap between the proximal support section and the distal access catheter.

2. The system of claim 1, wherein the elongated shape of the distal expanded section is cylindrical.

3. The system of claim 1, wherein the proximal surface and the distal surface taper in a substantially symmetrical manner.

4. The system of claim 1, further comprising the distal access catheter.

5. The system of claim 4, further comprising the guidewire.

6. The system of claim 1, wherein the distal expanded section, without the proximal surface and the distal surface, has a length of about 6-10 cm.

7. The system of claim 1, wherein the distal surface has an axial length of about 4-6 cm.

8. The system of claim 1, wherein the second outer diameter of the inner guide member is about 0.058-0.075 inches.

9. The system of claim 1, further comprising a cylindrically-shaped distal tip region that extends distally of the distal surface and forms a distal opening of the guidewire passage.

10. The system of claim 1, wherein the inner guide member further comprises a distal tip section distal to the distal expanded section and having a third outer diameter less than the second outer diameter of the distal expanded section.

11. A system for accessing vasculature of a patient, comprising:
  an inner guide member having a proximal support section, a distal expanded section located distally of the proximal support section, a distal tip portion located distally of the distal expanded section, and a guidewire passage extending between a proximal end and distal end of the inner guide member;
  the proximal support section having a first outer diameter;
  the distal expanded section having a second outer diameter that is larger than the first outer diameter of the proximal support section;
  the distal expanded section comprising an elongated shape with a proximal surface and a distal surface that taper in diameter in a substantially uniform manner; and,
  the distal tip portion having a cylindrical shape forming a distal opening of the guidewire passage;
  where in an operational configuration, the proximal end of the inner guide member is external to the patient and is slidable relative to a distal access catheter and to a guidewire positioned through the guidewire passage,
  where in the operational configuration the proximal surface of the distal expanded section is within the distal access catheter and the distal surface of the distal expanded section is outside of the distal access catheter such that as the distal access catheter is advanced within the patient, a first gap between the distal expanded section and the distal access catheter is less than a second gap between the proximal support section and the distal access catheter.

12. The system of claim 11, wherein the proximal surface and the distal surface taper in a substantially symmetrical manner.

13. The system of claim 11, further comprising the distal access catheter.

14. The system of claim 13, further comprising the guidewire.

15. The system of claim 11, wherein the distal expanded section, without the proximal surface and the distal surface, has a length of about 6-10 cm.

16. The system of claim 11, wherein the distal surface has an axial length of about 4-6 cm.

17. The system of claim 11, wherein the second outer diameter of the inner guide member is about 0.058-0.075 inches.

18. A system for accessing vasculature of a patient, comprising:

an inner guide member having a proximal support section, a distal expanded section located distally of the proximal support section, and a guidewire passage extending between a proximal end and distal end of the inner guide member;

the proximal support section having a first outer diameter;

the distal expanded section having a second outer diameter that is larger than the first outer diameter of the proximal support section; and, the distal expanded section comprising an elongated shape with a proximal surface and a distal surface that taper in diameter in a substantially uniform manner;

wherein the proximal end of the inner guide member is directly proximally accessible by a physician when the inner guide member is located within a distal access catheter to enable torsional and coaxial movement directly by the physician relative to the distal access catheter and to a guidewire positioned through the guidewire passage while maintaining the proximal surface within the distal access catheter and the distal surface outside of the distal access catheter, thereby minimizing a gap between the distal expanded section and the distal access catheter.

19. The system of claim 18, further comprising the distal access catheter.

20. The system of claim 19, further comprising the guidewire.

* * * * *